US008736439B1

(12) United States Patent
Shinozuka

(10) Patent No.: US 8,736,439 B1
(45) Date of Patent: May 27, 2014

(54) SOCK FOR BED-DEPARTURE DETECTION

(71) Applicant: Kenneth Feng Shinozuka, New York, NY (US)

(72) Inventor: Kenneth Feng Shinozuka, New York, NY (US)

( * ) Notice: Subject to any disclaimer, the term of this patent is extended or adjusted under 35 U.S.C. 154(b) by 0 days.

(21) Appl. No.: 13/858,017

(22) Filed: Apr. 6, 2013

(51) Int. Cl.
| G08B 1/08 | (2006.01) |
| G08B 13/14 | (2006.01) |
| G08B 23/00 | (2006.01) |
| A61B 5/103 | (2006.01) |
| A61B 5/117 | (2006.01) |

(52) U.S. Cl.
USPC .............. 340/539.11; 340/539.12; 340/572.1; 340/573.1; 600/595; 600/592; 600/587

(58) Field of Classification Search
USPC .......................... 340/539.11, 12, 572.1, 573.1
See application file for complete search history.

(56) References Cited

U.S. PATENT DOCUMENTS

| 4,736,312 | A | | 4/1988 | Dassler et al. |
| 4,907,845 | A | * | 3/1990 | Wood .......................... 340/573.4 |
| 5,221,088 | A | | 6/1993 | McTeigue et al. |
| 5,276,432 | A | | 1/1994 | Travis |
| 5,343,445 | A | | 8/1994 | Cherdak |
| 5,452,269 | A | | 9/1995 | Cherdak |
| 5,471,405 | A | | 11/1995 | Marsh |
| 5,523,741 | A | * | 6/1996 | Cane .......................... 340/573.1 |
| 5,914,659 | A | * | 6/1999 | Herman et al. ............ 340/573.1 |
| 6,122,846 | A | | 9/2000 | Gray et al. |
| 6,360,597 | B1 | | 3/2002 | Hubbard, Jr. |
| 7,632,239 | B2 | * | 12/2009 | Dar et al. ...................... 600/592 |
| 8,280,681 | B2 | | 10/2012 | Vock et al. |
| 2004/0173220 | A1 | * | 9/2004 | Harry et al. .................... 128/892 |
| 2007/0159332 | A1 | * | 7/2007 | Koblasz ...................... 340/572.1 |
| 2008/0001735 | A1 | * | 1/2008 | Tran .......................... 340/539.22 |
| 2008/0108913 | A1 | * | 5/2008 | Lengsfeld et al. ............ 600/595 |
| 2009/0178305 | A1 | * | 7/2009 | Maxwell et al. ................ 36/139 |
| 2010/0052897 | A1 | * | 3/2010 | Allen et al. ............... 340/539.12 |

(Continued)

FOREIGN PATENT DOCUMENTS

| JP | 2-280733 | 11/1990 |
| JP | 3093745 | 7/2000 |
| JP | 3322632 | 6/2002 |

OTHER PUBLICATIONS

Burridge et al., Phase II Trial to Evaluate the Actigait Implanted Drop-Foot Stimulator in Established Hemiplegia, J Rehabil Med 2007; 39: 212-218, all pages.*

(Continued)

*Primary Examiner* — Daniel Wu
*Assistant Examiner* — Emily C Terrell
(74) *Attorney, Agent, or Firm* — Morrison & Foerster LLP

(57) ABSTRACT

This invention is a method and apparatus for low-cost detection and alerting of bed-departure, which causes significant stress to caretakers of patients who often wander out of bed as a result of their dementia, Alzheimer's, or other medical conditions. The apparatus comprises a sock embedded with a pressure sensor and a battery-powered microcontroller unit with a radio frequency module. Once the user wanders out of bed and steps onto the floor, the sensor on the sock will immediately detect the pressure caused by his or her body weight and wirelessly trigger an audible sound at a caretaker's monitoring unit, which can be a smart phone or PC. The sensor and the microcontroller unit can be packaged in one assembly to be mounted on an ordinary sock, slipper, or shoe. The apparatus also accurately counts steps and measures the time interval between them.

11 Claims, 3 Drawing Sheets

(56) References Cited

U.S. PATENT DOCUMENTS

| | | | |
|---|---|---|---|
| 2010/0063779 A1* | 3/2010 | Schrock et al. | 702/188 |
| 2011/0054359 A1* | 3/2011 | Sazonov et al. | 600/595 |
| 2011/0245633 A1* | 10/2011 | Goldberg et al. | 600/301 |
| 2012/0253234 A1* | 10/2012 | Yang et al. | 600/595 |
| 2013/0013026 A1* | 1/2013 | Hoyer et al. | 607/49 |
| 2013/0176126 A1* | 7/2013 | Dunham | 340/573.1 |
| 2013/0185003 A1* | 7/2013 | Carbeck et al. | 702/41 |
| 2013/0211474 A1* | 8/2013 | Nielsen et al. | 607/49 |

OTHER PUBLICATIONS

"Sensor Sock: measuring your sole," dated Jul. 2, 2010, updated Oct. 14, 2011, available at www.CSIRO.au, printed on Dec. 10, 2013.

* cited by examiner

SOCK FOR BED-DEPARTURE DETECTION

CROSS-REFERENCE TO RELATED APPLICATIONS

Not applicable

STATEMENT REGARDING FEDERALLY SPONSORED RESEARCH OR DEVELOPMENT

Not applicable

REFERENCE TO SEQUENCE LISTING, A TABLE, OR A COMPUTER PROGRAM LISTING COMPACT DISC APPENDIX

Not applicable

BACKGROUND OF THE INVENTION

1. Field of the Invention

The present invention relates to a method and an apparatus for detecting and alerting of patients' bed-departure using a sock embedded with a pressure sensor and a microcontroller unit to trigger an alert on a caretaker's monitoring unit.

2. Description of the Prior Art

The population of seniors who suffer from Alzheimer's, dementia, and other medical conditions has increased in recent years. Their frequent accidents and injuries as a result of wandering out of bed cause significant stress to their caretakers at home as well as those in hospitals and nursing facilities. There is an increasing need for detecting and alerting of such bed departures to protect the safety of these patients and reduce the stress of their caretakers.

Prior art has used load sensors installed on a patient's bed to detect his or her bed departure. The art disclosed in patent document 1 uses weight information to determine whether a user is still on the bed or has left the bed. The arts disclosed in patent documents 2 to 4 calculate the center of gravity from the weight information of four points on the bed, and use the center-of-gravity position information to monitor the movement of a user in bed.

All of the prior art inventions for bed-departure detection require specialized beds installed with load sensors. The associated costs and cumbersome set-up prevent their wide applications in homes as well as in nursing facilities and hospitals.

On the other hand, there are patent and non-patent prior art on shoes and socks embedded with sensors. The art disclosed in patent documents 5 through 9 and patent document 12 use pressure sensors on athletic shoes to measure strides length, running speed and other stride characteristics for sport training purposes. The art disclosed in patent document 10 uses strain sensors on a shoe to monitor patient force during rehabilitation. The art disclosed in patent document 11 uses force sensors on a shoe insole for remote gait analysis. The non-patent document 1 is a sensor sock for measuring plantar pressure used in the diagnosis of peripheral neuropathy. None of the prior arts on shoes or socks with sensors addresses the needs for detecting bed-departure of wondering patients.

Prior Arts on Bed-Departure Detection:
Patent Document 1: Japanese Laid-Open Patent Application No. 2-280733
Patent Document 2: Japanese Patent No. 3093745
Patent Document 3: Japanese Patent No. 3322632
Patent Document 4: U.S. Pat. No. 5,276,432

Prior Arts on Shoes, Insoles, and Socks with Pressure/Force Sensors
Patent Document 5: U.S. Pat. No. 4,736,312
Patent Document 6: U.S. Pat. No. 5,221,088
Patent Document 7: U.S. Pat. No. 5,343,445
Patent Document 8: U.S. Pat. No. 5,452,269
Patent Document 9: U.S. Pat. No. 5,471,405
Patent Document 10: U.S. Pat. No. 6,122,846
Patent Document 11: U.S. Pat. No. 6,360,597
Patent Document 12: U.S. Pat. No. 8,280,681
Non-Patent Document 1: Sensor Sock, www.csiro.au.

BRIEF SUMMARY OF THE INVENTION

The present invention provides a simple method and a low-cost apparatus to detect and alert the bed-departure of wandering patients who suffer from Alzheimer's, dementia, or other medical conditions.

The apparatus comprises a pressure sensor embedded in a sock, a battery-powered microcontroller unit mounted on the sock, and a separate monitoring unit. The microcontroller unit continuously acquires an output signal from the pressure sensor at a predetermined time interval and compares the sensor signal with a predetermined threshold. Once the sock user wanders out of bed and steps onto the floor, his or her body weight will exert pressure on the sock, causing the sensor output signal to exceed the predetermined threshold. In response, the microcontroller unit immediately issues an alert by transmitting a radio-frequency signal to the caretaker's monitoring unit, such as a smart-phone, a PC, or a custom-made monitor. This signal triggers an audible sound out of the monitoring unit. The time of the alert is recorded into a database in the monitoring unit for the patent long-term health monitoring and care usages.

In another embodiment, the sensor and the microcontroller unit is packaged into one removable and re-mountable assembly to be mounted on an ordinary sock, slipper, or shoe.

Furthermore, the apparatus of the present invention accurately counts steps and measures the time interval between them. The results may be displayed on the microcontroller unit and/or wirelessly transmitted to a smart-phone or PC for further analysis and database purposes. This provides a simple and accurate method for monitoring and quantitative evaluation of the user's gait characteristics, an important indicator of his or her health conditions.

The present invention offers advantages over prior arts, as summarized below:
1. The method for bed-departure detection and alerting is simple and reliable;
2. The method for counting steps is accurate and reliable;
3. The cost of the apparatus is low;
4. The apparatus is easy to set up and operate.

These and other features and advantages of the present invention will become apparent to those of ordinary skill in the art from the following description and accompanying drawings, which describe, for purposes of illustration only, a preferred embodiment of the present invention.

DETAILED DESCRIPTION OF THE INVENTION

The apparatus according to the present invention comprises a pressure sensor embedded in the sole of a sock, a battery-powered microcontroller unit mounted on the same sock, and a separate monitoring unit to generate an audible sound, once wirelessly triggered by the microcontroller unit. This is illustrated in FIG. 1.

Figure 1:
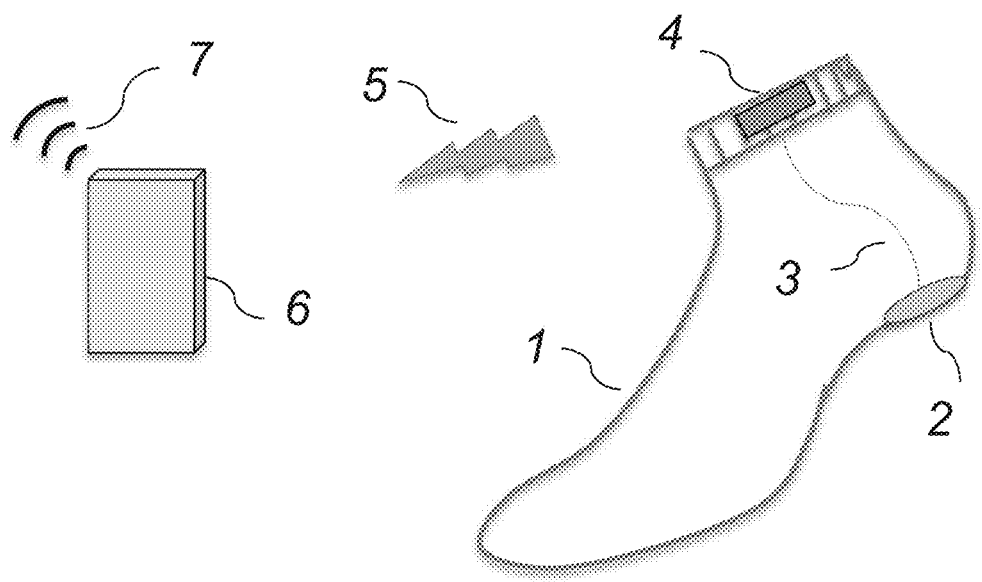
FIG. 1 is a schematic view, showing a preferred embodiment of the apparatus for detecting bed-departure in accordance with the present invention.

In FIG. 1, the sock is denoted by numeral 1, the pressure sensor by numeral 2, electrical wires by numeral 3, the microcontroller unit by numeral 4. Numeral 5 represents the wireless radio-frequency signal. Numeral 6 is the monitoring unit, which can be a smart-phone, a PC, or a custom-made monitor. Monitoring unit 6 has a radio-frequency module and a speaker. Numeral 7 represents the audible sound from the speaker of monitoring unit 6.

Figure 2:
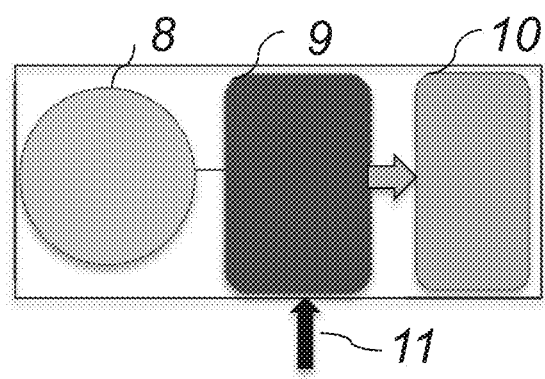
FIG. 2 is a schematic view, showing a preferred embodiment of the microcontroller unit.

FIG. 2 is a schematic view of a preferred embodiment of microcontroller unit 4, comprising a battery cell denoted by numeral 8, a microcontroller denoted by numeral 9, a radio-frequency module denoted by numeral 10, and sensor output signal by numeral 11.

Pressure sensor 2 is embedded in the sole of sock 1, connected by electrical wires 3 to microprocessor unit 4, which is mounted on sock 1. When the sock user is in bed, microcontroller 9 continuously acquires output signal 11 from sensor 2 and compares the signal with a predetermined threshold at each predetermined time interval. If the value of the sensor signal is less than the threshold, microcontroller 9 will continue acquiring a sensor output signal at the next time interval. Once the user wanders out of bed and steps onto the floor, his or her body weight will exert pressure on the sock, causing the sensor signal to exceed the predetermined threshold. The microcontroller will then command the radio-frequency module 10 to immediately transmit a radio-frequency signal 5 to the separate monitoring unit 6. Signal 5 will trigger an audible sound out of the monitoring unit 6 to alert a caretaker. The monitoring unit can be a smart-phone, a PC, or a custom-made monitor, each comprising a radio-frequency module and a speaker.

The time of the alert is recorded into a database in the monitoring unit for the patient health monitoring and care usages.

Pressure sensor 2 is any pressure sensor that can be embedded in the sole of a sock and is thin and soft enough not to affect walking.

Figure 5:
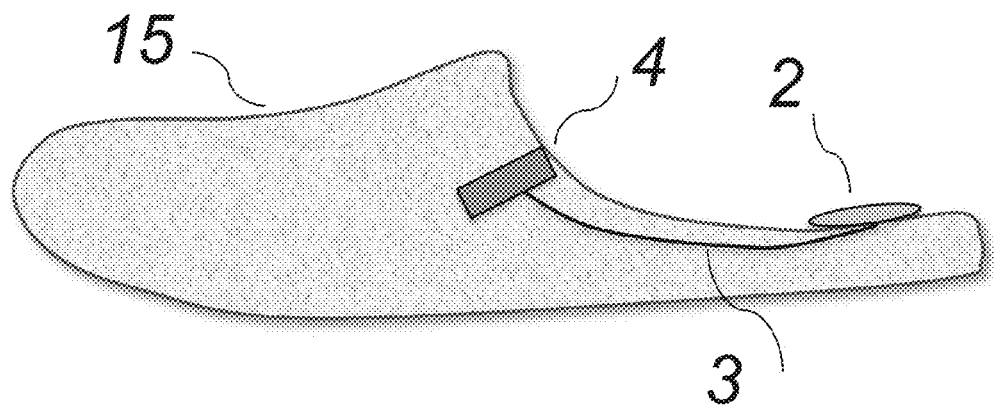
FIG. 5 is a schematic of the apparatus for detecting bed-departure according to an embodiment of the present disclosure.
Figure 6:
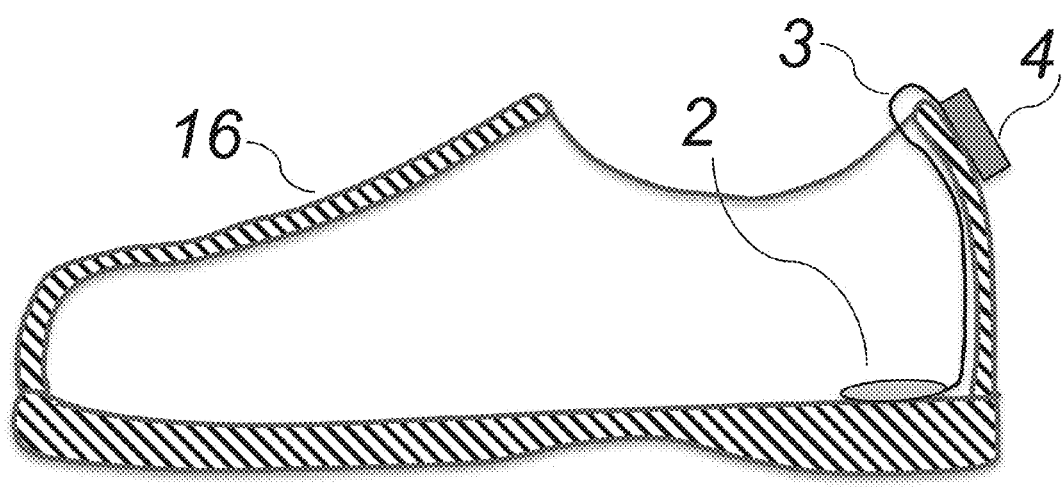
FIG. 6 is a schematic of the apparatus for detecting bed-departure according to an embodiment of the present disclosure.

Instead of a sock, pressure sensor 2 can be embedded in the insole of a slipper or the insole of a shoe, and microcontroller unit 4 is also mounted on the same slipper or the same shoe. A slipper 15 is illustrated in FIG. 5, and a shoe 16 is illustrated in FIG. 6. When a user in bed gets out of bed and steps his or her foot into the slipper or shoe on the floor, radiofrequency module in microcontroller 4 will immediately send a radiofrequency signal to trigger an audible sound out of monitoring unit 6 to alert the caretaker.

Figure 3:
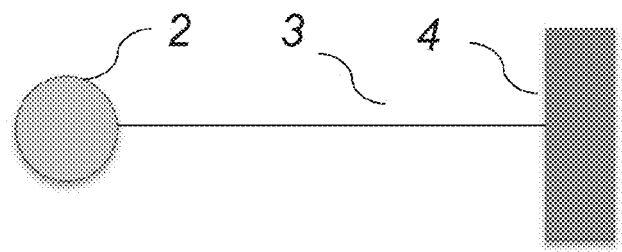
FIG. 3 is a schematic view, showing the sensor-microprocessor assembly.

In another embodiment of the apparatus as illustrated in FIG. 3, pressure sensor 2 and microcontroller unit 4, connected by electrical wires 3, are packaged into one assembly, which can be conveniently mounted on any ordinary sock, slipper, or shoe, with pressure sensor 2 in contact with the sole of a user's foot when in use. The advantage of this removable and re-mountable assembly is in its flexibility to be mounted on any ordinary footwear.

By adding a simple display screen to microcontroller unit 4, and programming an algorithm into microcontroller 9, the apparatus of the present invention for bed-departure detection becomes a pedometer, which accurately counts the number of steps taken in a given time period, measures the time interval between steps, and displays the results. The user may wear sock 1 embedded with pressure sensor 2 or any ordinary sock or shoe mounted with the sensor-microcontroller assembly shown in FIG. 3. Once microcontroller unit 4 is turned on, output signal 11 from pressure sensor 2 is continuously recorded into the memory of microcontroller 9 at each time interval for a given period of time. In the end of the period, the number of total steps and the average time interval between steps are computed in the microcontroller 9 and displayed in the display screen.

Figure 4:
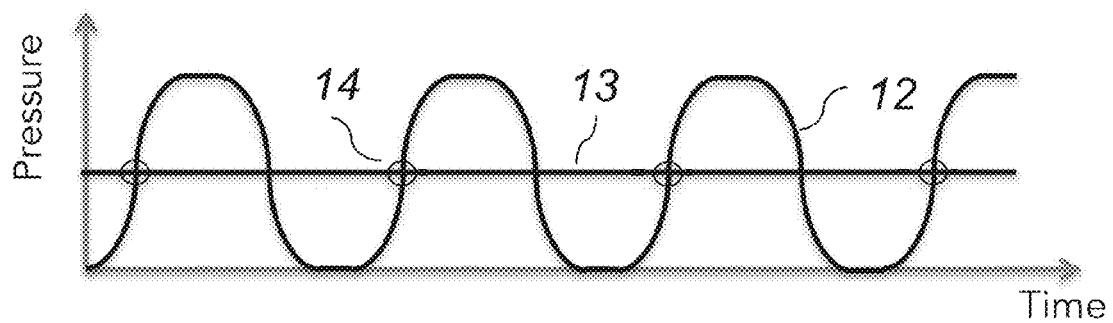
FIG. 4 is a schematic view of a plot of pressure time history measured during walking or running, showing how steps are counted and the time intervals measured.

To demonstrate how steps are counted and the time interval between them are measured, FIG. 4 schematically plots a pressure time history measured on one foot during walking or running. In FIG. 4, the horizontal axis is time and the vertical axis is pressure measured by the pressure sensor. One cycle represents the change of pressure on the single foot during one step, where the minimum pressure value occurs when the foot is off the ground and the maximum value occurs when the foot is stepping on the ground. Numeral 12 denotes a pressure value at a time instant, numeral 13 denotes a predetermined threshold, and numeral 14 denotes an intersection where pressure output signal 12 increases and exceeds threshold 13. Because the plot is the pressure time history on a single foot, each time when sensor output signal 12 increases and exceeds threshold 13 at intersection 14, two steps are counted. The time duration between two adjacent said intersections is a half of the time interval between steps. An average time interval of steps for the entire monitoring period may be computed by averaging each of the measured time intervals.

When needed, the recorded pressure time history data, as well as the number of steps and the average time interval between steps are transmitted to a smart-phone or a PC via radio-frequency module 10 for further analysis and database purposes. These data can be analyzed and made into a database, useful for monitoring and quantitative evaluation of the user's gait characteristics, as they reveal important information about his or her health conditions.

The method and apparatus of the present invention offer significant advantages over the prior art. The method for bed-departure detection is simple and reliable. The cost of the apparatus is low. It is easy to set up and operate the apparatus. The method for counting steps and measuring the time interval between steps is more accurate and reliable, compared to widely available pedometers, which are inaccurate because they use accelerometers to measure hip motion to count steps, rather than measuring the steps themselves.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent elements or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

I claim:

1. A method of detecting bed-departure, comprising the following steps:
    having a user in bed wear a sock, which is embedded or mounted with a pressure sensor in the sole, and mounted with a microcontroller unit comprising a battery, a radio-frequency module, and a microcontroller connected to said pressure sensor, or placing a slipper or a shoe on the floor near a user's bed, wherein the slipper or shoe is embedded or mounted with a pressure sensor in the sole, and mounted with a microcontroller unit comprising a battery, a radio-frequency module, and a microcontroller connected to said pressure sensor;
    switching on said microcontroller unit to acquire a sensor output signal at a predetermined time interval;
    having said microcontroller compare the value of said sensor output signal with a predetermined threshold at said predetermined time interval;
    if said sensor output signal value is less than said threshold, having said microcontroller continue to acquire a new sensor output signal at the next time interval;
    if said sensor output signal value is equal or larger than said threshold, having said radio-frequency module transmit a radio-frequency signal to a separate monitoring unit; and
    having said monitoring unit generate an audible sound as an alert, once receiving said radio-frequency signal.

2. The method of claim 1, further comprising recording the time of said alert into a database in the memory of said monitoring unit.

3. The method of claim 1, wherein said alert is triggered when said user wanders out of bed.

4. The method of claim 1, wherein said pressure sensor and said microcontroller unit connected to said pressure sensor are packaged in one removable and re-mountable assembly, which is mounted on said sock, with said pressure sensor on the sole of said sock.

5. The method of claim 1, wherein said pressure sensor and said microcontroller unit connected to said pressure sensor are packaged in one removable and re-mountable assembly, which is mounted on said slipper or shoe, with said pressure sensor on the insole of said slipper or on the insole of said shoe.

6. An apparatus for detecting bed-departure, comprising:
    a pressure sensor embedded in or mounted on the sole of a sock worn by a user in bed, or a pressure sensor embedded in or mounted on the insole of a slipper or a shoe placed on the floor near a user's bed;
    a microcontroller unit mounted on said sock or said slipper or shoe, said microcontroller unit comprising a battery, a radio-frequency module, and a microcontroller connected to said pressure sensor; and
    a monitoring unit, which is a smart-phone, a PC, or a custom-made monitor, said monitoring unit comprising a radio-frequency module and a speaker,
    wherein said microcontroller is configured to be switched on to acquire an output signal from said pressure sensor at a predetermined time interval, wherein said microcontroller compares said sensor signal with a predetermined threshold at the predetermined time interval and, when said sensor output signal value is equal or larger than said threshold, commands said radio-frequency module to transmit a radio-frequency signal to trigger an audible sound out of said monitoring unit.

7. The apparatus of claim 6, wherein said pressure sensor and said microcontroller unit connected to said pressure sensor are packaged into a removable and re-mountable assembly, which is mounted on said slipper or shoe, with said pressure sensor on the insole of said slipper or shoe.

8. The apparatus of claim 6, wherein said pressure sensor and said microcontroller unit connected to said pressure sensor are packaged into a removable and re-mountable assembly, which is mounted on said sock, with said pressure sensor on the sole of said sock.

9. The method of claim 1, wherein said alert is triggered when said user steps onto the floor.

10. The method of claim 1, wherein said alert is triggered when said user steps his or her foot into said slipper or said shoe placed on the floor.

11. The apparatus of claim 6, wherein said monitoring unit is a caretaker's monitoring unit.

\* \* \* \* \*